(12) United States Patent
Klepp (10) Patent No.: US 8,401,630 B2
(45) Date of Patent: Mar. 19, 2013

(54) METHOD OF DETERMINING TRAINING INTENSITY

(75) Inventor: Nikolaus Klepp, Gmunden (AT)

(73) Assignee: PULSE7 GmbH (AT)

( * ) Notice: Subject to any disclaimer, the term of this patent is extended or adjusted under 35 U.S.C. 154(b) by 630 days.

(21) Appl. No.: 12/526,114

(22) PCT Filed: Feb. 5, 2008

(86) PCT No.: PCT/AT2008/000037
§ 371 (c)(1),
(2), (4) Date: Mar. 4, 2010

(87) PCT Pub. No.: WO2008/095213
PCT Pub. Date: Aug. 14, 2008

(65) Prior Publication Data
US 2010/0217142 A1    Aug. 26, 2010

(30) Foreign Application Priority Data
Feb. 6, 2007   (AT) .................................. A 195/2007

(51) Int. Cl.
*A61B 5/0452*    (2006.01)
(52) U.S. Cl. ........................................................ 600/520
(58) Field of Classification Search .................... 600/520
See application file for complete search history.

(56) References Cited

U.S. PATENT DOCUMENTS
6,454,679 B1 * 9/2002 Radow ............................... 482/4

FOREIGN PATENT DOCUMENTS

| DE | 69532803 T2 | 2/2005 |
| DE | 102004052083 A1 | 5/2006 |
| DE | 60115301 T2 | 6/2006 |
| EP | 1127543 A1 | 8/2001 |
| WO | 9620640 A1 | 7/1996 |
| WO | 03053233 A1 | 7/2003 |

OTHER PUBLICATIONS

International Search Report, PCT/AT2008/000037, dated Jul. 4, 2008.
Michaelm Brennan et al: "Do Existing Measures of Poincaré Plot Geometry Reflect Nonlinear Features of Heart Rate Variability?" IEEE Transactions on Biomedical Engineering, IEEE Service Center, Piscataway, NJ, 115, vol. 48, No. 11, Nov. 1, 2001, XP011007162 ISSN: 0018-9294.

(Continued)

*Primary Examiner* — Eric D. Bertram
(74) *Attorney, Agent, or Firm* — Lerner, David, Littenberg, Krumholz & Mentlik, LLP (57) ABSTRACT

Method of determining the training intensity of a person (2), whereby time intervals $RR_i$ (13) between consecutive heartbeats are recorded whereupon from sequences of these time intervals $RR_i$ (13) a sequence of standardised intervals $rr_i$ (14) is generated through mathematical modelling. From two consecutive standardised intervals $rr_i$ (14) and $rr_{i+1}$ points in a Poincaré plot are generated and with regard to the principal horizontal axis $X_0$ (16) of a confidence ellipse of these points a standard deviation $SO_L$ is calculated. From pairs of values formed of a mean value $RR_{MV}$ of the sequence of intervals $RR_i$ (13) and the standard deviation $SO_L$ for further sequences of standardised intervals $rr_i$ (14) a training intensity curve (20) is then produced for the person (2) whereby the training intensity curve (20) is produced from pairs of values of the heart frequencies HF ($HF=1/RR_{MV}$) corresponding to the mean values $RR_{MV}$ and the standard deviations $SO_L$.

19 Claims, 4 Drawing Sheets

OTHER PUBLICATIONS

Horn, A., Diagnostik der Herzfrequenzvariabilitat in der Sportmedizin Rahmenbedingungen und methodische Grundlagen. Dissertation Ruhr-Universitat Bochum Dezember 2003 [retrieved on Aug. 13, 2007)]. Retrieved from the Internet: URL:http://deposit.ddb.de/cgi•bin/dokserv?idn=972276742&dokvar=d1&dok_ext=pdf&filename=972276742.pdf KapiteIII.2.1, III.3.1.1-2, XI.

* cited by examiner

METHOD OF DETERMINING TRAINING INTENSITY

CROSS REFERENCE TO RELATED APPLICATIONS

The present application is a national phase entry under 35 U.S.C. §371 of International Application No. PCT/AT2008/000037, filed Feb. 5, 2008, published in German, which claims the benefit of Austrian Patent Application No. A 195/2007, filed Feb. 6, 2007. The disclosures of said applications are incorporated by reference herein.

The invention relates to a method and device for determining the stress intensity/training intensity of person, whereby the heart frequency data of the person is measured in accordance with the features of the introduction sections of claims 1, 2 and 19.

For sports medicine applications in particular, the question of the optimum training/stress intensity of a training person is of central importance. However, pure heart rate performance tests are completely unsuitable for this as the heart rate is approximately proportional to the stress intensity and an optimum training level cannot be determined from this. This level differs between individuals and can only be determined via the lactate concentration in the blood. Lactate, the end product of anaerobic lactadic metabolisation is the best indicator for an objective assessment of endurance capacity. It is formed if during intensive endurance stress the oxygen taken up through breathing is not quite sufficient to cover the energy required in the muscle for muscle contraction. During period of stress lactate is formed constantly but also eliminated again so that with increasing intensity a lactate concentration is reached at which formation still just corresponds to elimination. In sports medicine this range is known as maximum lactate steady state (maxlass), as the aerobic/anaerobic threshold or lipometabolism. A reliable assessment and control of endurance capacity is therefore only possible through knowing the blood lactate concentrations at different physical stress levels, i.e. knowledge of the individual metabolic situation. Test methods that only relate the heart frequency to performance are not suitable for determining the optimum training level.

However, in order to be able to determine the course of an individual's blood lactate concentration at various stress levels laborious tests with accompanying blood sampling and analyses are required. But for concurrent measurement during training such measurements are completely impractical. Tests were therefore carried out to develop methods that allow non-invasive estimation of the lactate content in the body in relation to physical exertion. One such method is described in document EP 1 127 543 B1 for example, whereby the heart frequency data of a person are entered, along with parameters setting out the physiology of the person, into a mathematical model that models the lactate concentration in the body and provides an estimated value of the lactate concentration in the body of the training person. However, it has been shown that the physiological parameters used, such as age, weight, height and sex, as well as the entry of stress parameters such as the speed or resistance of an exercise cycle are not only insufficient for obtaining a reliable result, but that this is also a hindrance to user-friendly application in popular sports.

The aim of the present invention is therefore to create method and/or a device for determining the training intensity of a person, which on the basis of measurement of the heart frequency allows the optimum training intensity of a person to be determined.

This aim of the invention is achieved by the method in accordance with the method steps of claim 1. According to this, the method for determining the training intensity of a person envisages the measurement of heart frequency information, whereby initially the time intervals $RR_i$ between consecutive heartbeats are recorded. By defining a number N of consecutive intervals $RR_i$ or by determining an observation interval a sequence of intervals $RR_i$ is selected and from the sequence of these intervals $RR_i$ standardised intervals $rr_i$ are generated through mathematical modelling. Then, for each two consecutive standardised intervals $rr_i$ and $rr_{i+1}$ points are produced in a Poincaré plot of the standardised intervals $rr_i$ and by way of an orthogonal regression analysis a principal horizontal axis $X_0$ and a principal vertical axis $Y_0$ of the points in the sequence of the standardised intervals $rr_i$ in the Poincaré plot are determined. The standard deviation $SO_L$ is then calculated from the orthogonal distance of points from the principal horizontal axis $X_0$. As a result of this partial analysis a pair of values, consisting of a mean value $RR_{MV}$ the sequence of intervals $RR_i$ and standard deviation $SO_L$ is saved. The above analysis steps are continued for further sequences of intervals $RR_i$. From the thus determined pairs of values of heart frequencies HF ($HF=1/RR_{MV}$) corresponding to mean values $RR_{MV}$ and the standard deviations $SO_L$ a training intensity curve is then produced for the person. By comparing the most recently determined heart frequency HF with the determined training intensity curve, the current specific training intensity of the person is determined. What is advantageous in the method is the fact that monitoring concurrent with training and the determination of the optimum stress level of a training person are possible without prior laborious tests, such as blood sampling and determination of the blood lactate concentration for example.

The aim of the invention is also independently achieved by the method in accordance with the method steps of claim 2. Here, in addition to the method described above, as well as the standard deviation $SO_L$ from the orthogonal distances of the points of the sequence of standardised intervals $rr_i$ with regard to the principal vertical axis $Y_0$ another standard deviation $SO_W$ is also calculated. As a result of the partial analysis pairs of values consisting of a mean value $RR_{MV}$ of the sequence of intervals $RR_i$ and a quotient $s=SO_L/SO_W$ formed of standard deviation $SO_L$ and standard deviation $SO_W$ are stored. From the thus determined pairs of values a training intensity curve is produced for the person, and by comparing the most recently determined heart frequency with the determined training intensity curve the current, specific training intensity/physical stress level of the person is determined.

In accordance with a further development of the method it is envisaged that sequences of intervals $RR_i$ to be selected for analysis are chosen from two observation intervals that overlap in time. This has the advantage that a sufficiently large number of pairs of values for determining the training intensity curve is obtained relatively quickly so that reliable statements about the current training intensity can be made more rapidly.

Also advantageous are the further developments of the method in accordance with claims 6 and 9 as the reliability of the evaluation results can be improved therewith.

The embodiments in accordance with claims 10 to 15 have the advantage that with the training intensity curves with more strongly or clearly emphasised curve section can be obtained both in the upper as well as the lower exertion range. The optimum training range can therefore be determined more reliably.

The further development of the method in accordance with claim 16 has the advantage that through the used approximation of the training intensity curve an sufficiently good approximation is available based on experience.

Also advantageous is the further development of the method in accordance with claim 17 as it is associated with a training intensity curve that progresses in time and becomes more and more stable, as well as more reliable monitoring of the training and/or stress intensity.

In accordance with a further development of the method it is envisaged that on completion of the training the training intensity curve is saved along with data, such as the name of the person and the details of the completed training. This has the advantage of allowing subsequent comparisons to be made and conclusions to be drawn about longer-term developments in the performance capacity of a person.

The aim of the invention is also achieved independently by the device in accordance with claim 19 for monitoring the stress intensity of a person. It is envisaged that the device comprises a unit that can be attached to the body, with a sensor for recording heartbeats, whereby the device comprises an evaluation unit for implementing the method as described above, and an output unit for informing the person about the determined stress intensity.

The invention will be described below in more detail with the aid of the examples of embodiment set out in the drawings.

By way of introduction it is set out that in the various described examples of embodiment the same components are given the same reference number and the same component designations, whereby the disclosures contained in the entire description can accordingly be transferred to the same components with the same reference numbers and/or the same component designations. Position details selected in the description, such as, for example, top, bottom, at the side etc. relate to the figure being directly described and shown, and can be transferred according to a new position in the event of the position changing. Furthermore, individual features or combinations of features from the various shown and described examples of embodiment can in themselves represent solutions that are independent, inventive or relate to the invention.

Figure 1:
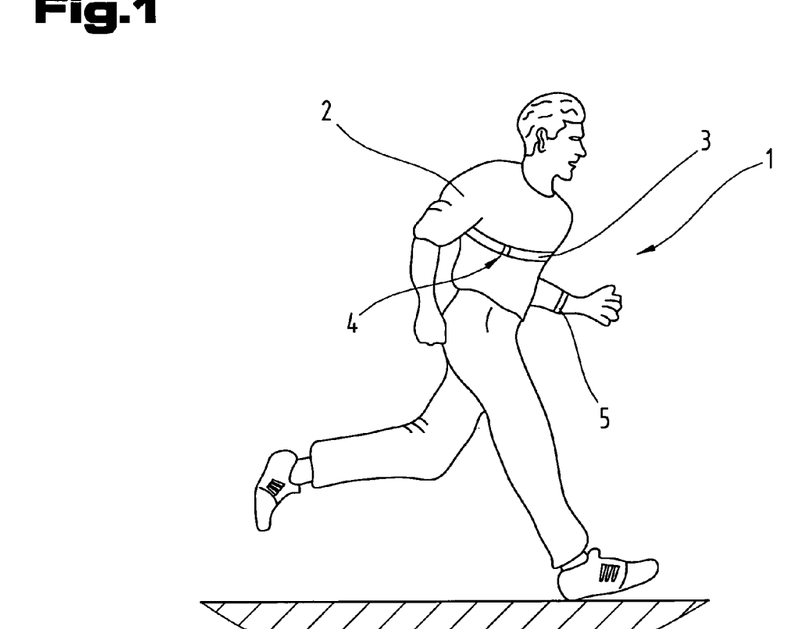
FIG. 1 shows a device which is attached to a training person in order to monitor the stress intensity.

FIG. 1 shows a device which is attached to a training person 2 in order to monitor the stress intensity.

In accordance with this example of embodiment the device 1 comprises a chest belt 3 which is equipped with a sensor 4 for recording heartbeats and with a monitoring unit 5, which is worn by the person 3 in a similar manner to a wristwatch.

The sensor 4 has electrodes so that in a known manner an electrocardiogram (ECG) of the heart activity of the person 2 can be recorded.

Figure 2:
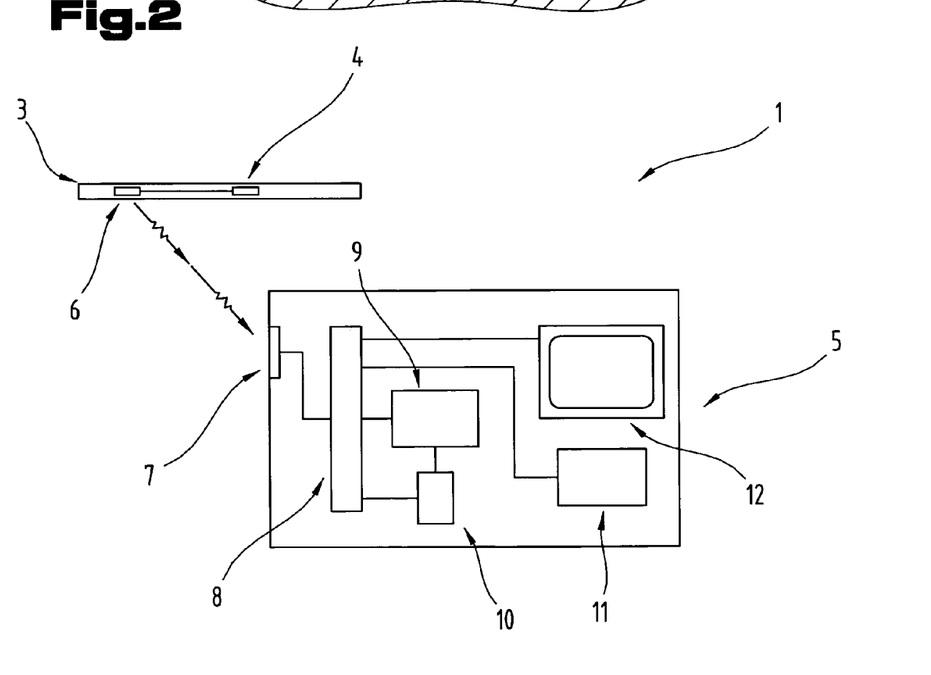
FIG. 2 sets out the principle of the chest belt and the monitoring unit of the device in accordance with FIG. 1.

FIG. 2 shows a simplified diagram of the principle of the chest belt 3 and the monitoring unit 5 of device 1.

In addition to the sensor 4, the chest belt 3 also has a transmitter 6 for transmitting the detected signals to the monitoring unit 5. This in turn has a receiver 7 as a signal input for the further processing of the heart frequency data. The monitoring unit also has a central control unit 8, an evaluation unit 9 and a memory 10 for saving or intermediately storing the recorded heart frequency data and/or the data to be calculated subsequent to evaluation. For operating the monitoring unit 5 an operating unit 11 is provided and for showing the results of data evaluation there is an output or display 12. For implementing the method according to the invention a computer program is loaded in the evaluation unit 8 and/or the central control unit 8.

In the evaluation unit 9, from the signals of the heart activity of the person 2 the time intervals of consecutive heartbeats are measured and saved in the memory 10.

With the aid of following FIGS. 3 to 6 a first example of embodiment of the method will now be described.

Figure 3:
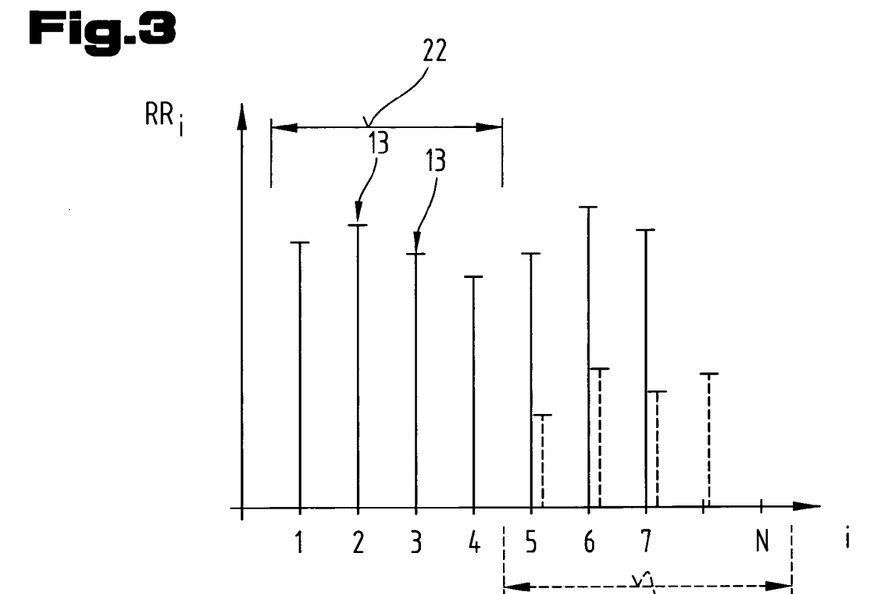
FIG. 3 shows a diagram with the values of the time intervals $RR_i$ of consecutive heartbeats.

FIG. 3 shows a diagram with intervals $RR_i$ 13 of consecutive heartbeats.

The time intervals between the individual heartbeats are represented by the number i on the X-axis and the interval $RR_i$ 13 on the Y-axis. The intervals $RR_i$ 13 are usually expressed in ms (milliseconds), i.e. as the time duration between two consecutive heartbeats. Alternatively it is also possible to use the current time of a heartbeat as the parameter to be entered on the X-axis instead of i. In the next processing step, from the continuously recorded intervals $RR_i$ 13 sequences of intervals $RR_i$ 13 are selected to serve as the basis of analyses of the variability of the heart frequency HF. The analysis takes place in discrete units, for example a fixed number of 150 intervals $RR_i$ 13 or of all heartbeats recorded within an observation interval of, for example, 1.5 minutes. Such a sequence of intervals $RR_i$ 13 is thus formed, for example, by a number of N=150 intervals $RR_i$ 13 (i=1 ... N) following on from each other in time.

Figure 4:
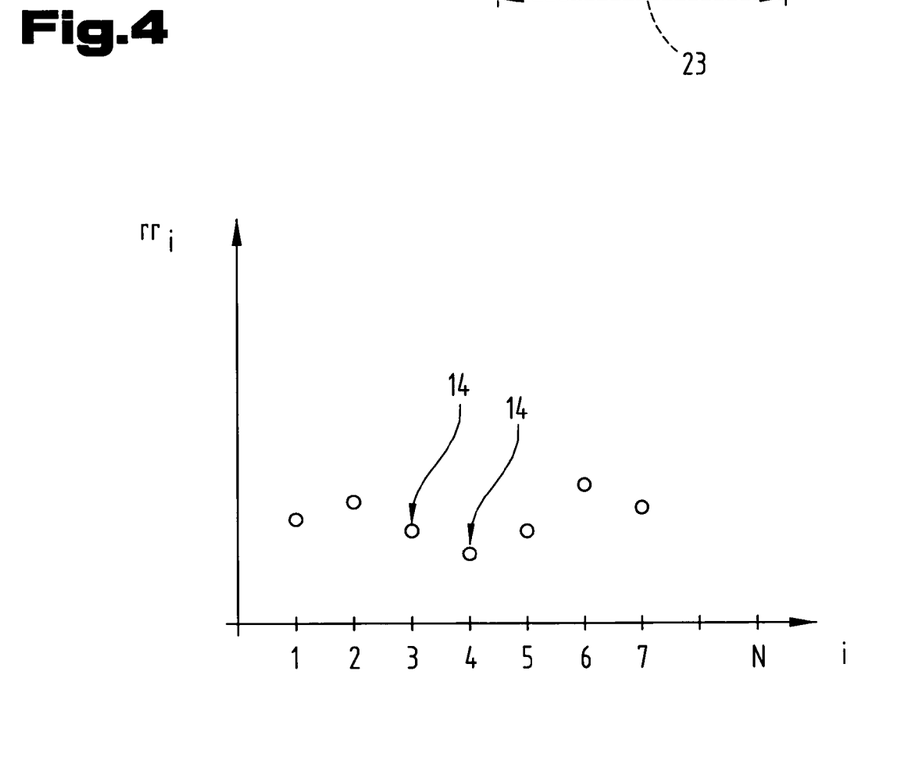
FIG. 4 shows a diagram of a sequence of standardised intervals $rr_i$.

In a next processing stage a sequence of standardised intervals $rr_i$ 14 is generated from the sequence of intervals $RR_i$ 13, as shown in FIG. 4. According to a first example of embodiment of the method the sequence of standardised intervals $rr_i$ 14 is created by each interval $RR_i$ 13 being divided by a mean value $RR_{MV}$ of the sequence of intervals $RR_i$ 13.

$$rr_i = RR_i / RR_{MV}; \; i=1 \ldots N$$

Whereas the intervals $RR_i$ 13 exhibit the dimensions of a period of time (normally expressed in ms), the standardised intervals $rr_i$ 14 represent dimensionless parameters.

Figure 5:
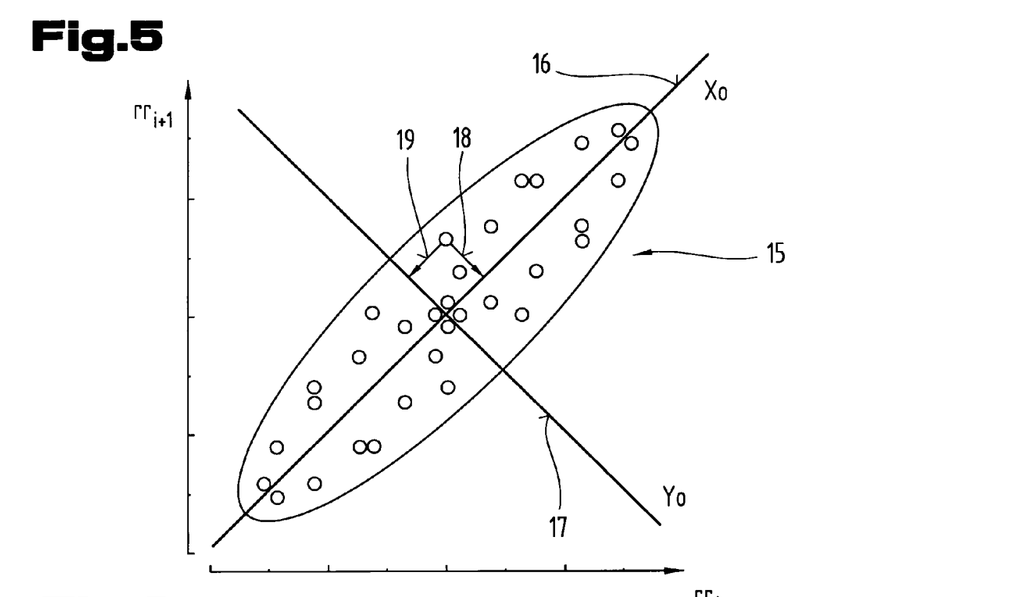
FIG. 5 shows a Poincaré plot of the standardised intervals $rr_i$.

FIG. 5 shows a Poincaré plot of the standardised intervals $rr_i$ 14.

In order to do this pairs of values of consecutive intervals $rr_i$ 14 and $rr_{i+1}$ are entered as points in the diagram in accordance with FIG. 5. In this two-dimensional graphic representation a cluster 15 is produced in which the variability of the heart frequency HF is expressed in a way that allows further quantitative analysis. The Poincaré plot of the standardised intervals $rr_i$ 14 can also be seen as a visualisation of the fact that consecutive heartbeats always differ in their duration, i.e. the length of the intervals $RR_i$ 13. In a next processing stage, for the points in the cluster 15 in the Poincaré plot, the computer program in the monitoring unit 5 calculates a principal horizontal axis $X_0$ 16 and a principal vertical axis $Y_0$ 17 of a so-called confidence ellipse, more particularly a 95% confidence ellipse. This can be done by means of regression analysis or orthogonal regression analysis methods. Therefore each point of the points cluster 15 is at an orthogonal distance 18 with regard to the principal horizontal axis $X_0$ 16 and at an orthogonal distance 19 with regard to the principal vertical axis $Y_0$ 17. In a further processing stage a standard deviation $SO_L$ is calculated from the orthogonal distances 18. This standard deviation $SO_L$ of the orthogonal distances 18 with regard to the principal horizontal axis $X_0$ 16 is stored together with the mean value $RR_{MV}$ of the sequence of intervals $RR_i$ 13 as the result of evaluation of the sequence of intervals $RR_i$ 13.

The processing stages described above are then carried out for further sequences of intervals $RR_i$ 13 and the corresponding values of the standard deviation $SO_L$ and the mean value $RR_{MV}$ of the sequence of intervals $RR_i$ 13 are recorded and/or saved. These pairs of values can be shown in a two-dimensional diagram whereby the heart frequency HF (i.e. the reciprocal value $HF=1/RR_{MV}$) corresponding to the mean value $RR_{MV}$ of the relevant sequences of intervals $RR_i$ 16 is entered on the X-axis, and the relevant standard deviation $SO_L$ is entered in the Y-axis (FIG. 6).

Figure 6:
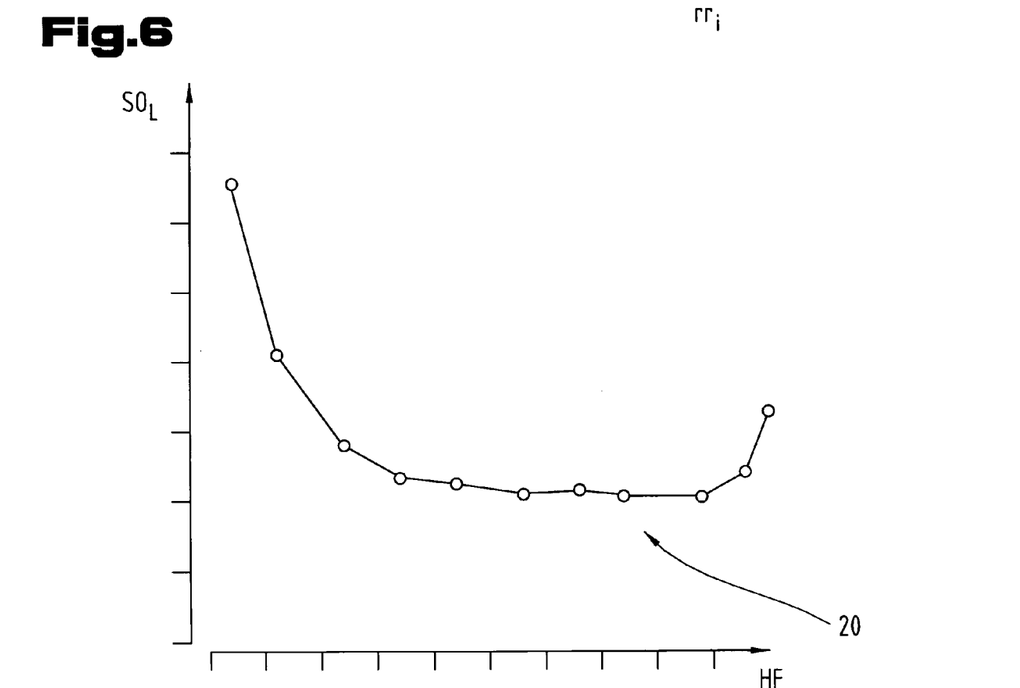
FIG. 6 shows a diagram of the standard deviations $SO_L$ at various stress intensities and/or different heart frequencies HF.

FIG. 6 shows a diagram of the standard deviations $SO_L$ at different stress intensities.

The pairs of values determined in accordance with the method described above from the means values $RR_{MW}$ and the relevant standard deviations $SO_L$ determine the characteristic stress intensity curve or training intensity curve 20 of the person 2 in question. As the heart frequency HF is known to be proportional to performance or stress intensity, the heart frequency HF values entered on the X-axis can be considered being equivalent to the stress intensity. The training intensity curve 20, as determined by the pairs of values of mean values $RR_{MV}$ and standard deviations $SO_L$ derived by the above method, shows characteristic features that are of great use in determining the current stress or training intensity of the person 2. Starting from a minimum in the training intensity curve 20 the standard deviations $SO_L$ show an increase at lower stresses and/or lower heart frequencies HF and also at higher stresses and/or higher heart frequencies HF. Studies show that the minimum standard deviation corresponds to around 70% of the output of the lactate steady state and lactate values of below 2 mmol/l as recommended for health-orientated endurance training are achieved.

Finally, the training intensity curve 20 allows the current specific training intensity of the person 2 to be determined in that the most recently determined values, i.e. the mean value $RR_{MV}$ of the sequence of intervals $RR_i$ 13 and the corresponding standard deviation $SO_L$ are compared with the course of the training intensity curve 20. In doing so it should be noted that when the device is used by the person 2 for the first time the training intensity curve 20 is not yet present and is produced gradually during progressive training and the associated evaluations by the monitoring unit 5 of heart frequency data of the person 2 through storage of the corresponding pairs of values, consisting of the mean values $RR_{MV}$ of the sequence of intervals $RR_i$ 13 and the corresponding standard deviations $SO_L$. The practical use of the device 1 by the person 2 takes place, for example, in that the person 2 initially starts to operate the monitoring unit 5 by means of the operating unit 11 and then starts to train with increasing exertion. As the duration of the training progresses points in the training intensity curve 20 in its descending arm or in the lower stress range are gradually calculated and recorded. As expected, during the course of on-going training the person 2 will gradually increase the exertion so that points in the training intensity curve 20 from the upper stress range can also be calculated. The training intensity curve 20 is therefore solely brought about through the alternating exertions of the training person 2 during ongoing training.

In accordance with the invention it is envisaged that the person 2 is informed by the monitoring unit 5 about the results of the comparison of the current values of the standard deviations $SO_L$ and/or the heart frequency HF in accordance with the mean value $RR_{MV}$ with the training intensity curve 20. This can take place, for example, through a graph corresponding to that in FIG. 6 being shown on the display 12 of the monitoring unit, in which the most recently determined values are specially highlighted. The person 2 has the possibility of reading off his/her current stress level in comparison with his/her own training intensity curve 20 and responding to this by increasing, decreasing or keeping the stress level the same. Alternatively it could also be envisaged that the monitoring unit 5 has an acoustic output that provides the persons 2 with relevant information about his/her current specific training intensity.

In order to carry out the analyses of the heart frequency data and evaluations of the data as envisaged by the method, appropriate algorithms are provided in the monitoring unit 5 and/or the computer program of the evaluation unit 9. The individual minimum of the standard deviation $SO_L$ takes place regression-analytically in which in accordance with the method of minimising the deviation squares a polynomial $SO_L$ (HF), preferably a third degree polynomial, is applied through the points of the training intensity curve 20. That is to say, the points of the training intensity curve 20 are approximated by the polynomial.

$$SO_L(HF)=s_0+s_1HF+s_2HF^2+s_3HF^3$$

On the basis of the regression-analytically determined polynomial $SO_L$ (HF), the minimum of the standard deviation $SO_L$ is then determined differential-analytically. In implementing the method it is also envisaged that the training intensity curve 20 calculated in this way and the polynomial $SO_L$(HF) are recalculated at regular intervals. Preferably, after each determination of a new pair of values of the most recently analysed sequence of intervals $RR_i$ 13, i.e. the most recently determined mean value $RR_{MV}$ of the sequence of intervals $RR_i$ 13 and the most recently determined corresponding standard deviation $SO_L$ a new calculation of the polynomial representing the training intensity curve 20 is carried out. As a result, through the gradual increase in the number of points in the diagram in accordance with FIG. 6 the course of the training curve 20 becomes gradually more stable and the monitoring of the training and stress intensity thereby comes more and more reliable.

Figure 7:
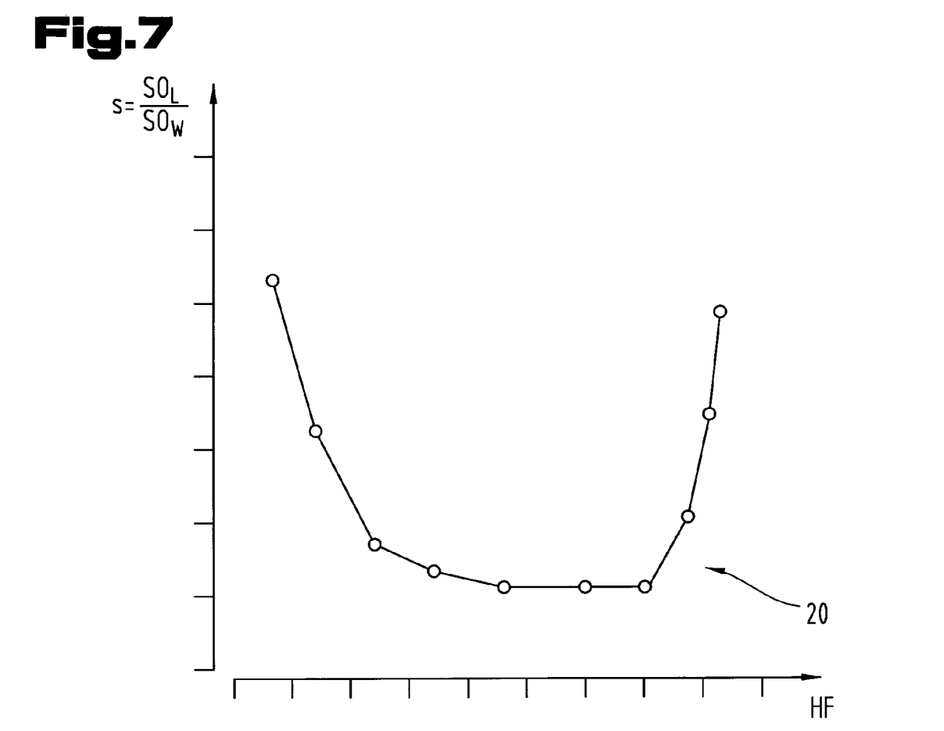
FIG. 7 shows an alternative example of embodiment of a training intensity curve.

With the aid of FIG. 7 an alternative example of a training intensity curve 20 is described. According to the representation of the points in the points cluster in the Poincaré plot in FIG. 5, in addition to the standard deviation $SO_L$, a standard deviation $SO_W$ is also calculated from the orthogonal distances 19 with regard to the principal vertical axis $Y_0$ 17. From the two standard deviations $SO_L$ and $SO_W$, through quotient formation, a new characteristic parameter is created, namely a quotient $s=SO_L/SO_W$. As the result of evaluation of a sequence of intervals $RR_i$ 13 the pair of values from the quotient s and the mean value $RR_{MV}$ is saved. These processing steps are carried out continuously for further sequences of intervals $RR_i$ 13 and the obtained values of the quotients $s=SO_L/SO_W$ and the mean value $RR_{MW}$ of the relevant sequences of intervals $RR_i$ 13 are recorded. These pairs of values can now also, as has been described above with regard to the standard deviation $SO_L$, be set out in a two-dimensional diagram. In the diagram in FIG. 7 the X-axis shows the mean value $RR_{MW}$ of the heart frequencies HF corresponding to the relevant sequences of intervals $RR_i$ 13 and the Y-axis shows the relevant characteristic parameter $s=SO_L/SO_W$ and in this way an alternative training intensity curve 20 is obtained. The points of this training intensity curve 20 can in turn be approximated by means of a polynomial $$s(HF)=u_0+u_1HF+u_2HF^2+u_3HF^3$$

The obtained training intensity curve 20 in accordance with FIG. 7 now also allows monitoring of the current training and/or stress intensity of a person 2 subject to alternating physical stress levels.

It should be emphasised that in the described method the desired result can be achieved through measurement of the intervals $RR_i$ 13. A prior examination of the person 2 to determine his/her individual performance characteristics is not necessary and can be dispensed with as these person-specific characteristics are automatically given through the above-described determination of the training intensity curve 20 on the basis of the current performance ability and/or daily constitution of the person 2. Prerecording of a training intensity curve 20 for subsequent used to assess the current training intensity is not only unnecessary but could even be disadvantageous as in consequence of a change in the daily constitution or changed performance level of the person 2 this could even lead to an incorrect assessment. By contrast, in accordance with the method, it is envisaged that on completion of training by the person 2, the thus obtained training intensity curve 20 is supplemented by corresponding entries in the operating unit 11 of the monitoring unit 5 in addition to data such as the name of the person 2 and the dates of the completed training being saved in the memory 10 of the monitoring unit 5. On the basis of subsequently carried out comparisons of the training intensity curves 20 of training carried out at larger time intervals this allows conclusions to be drawn on the long-term development of the physical performance capacity of the person.

Figure 8:
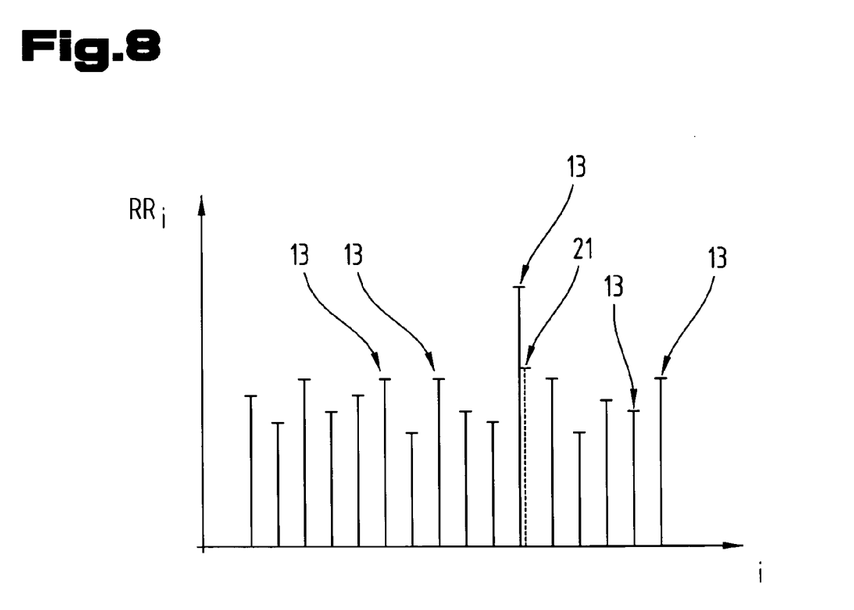
FIG. 8 shows a diagram of intervals $RR_i$ with an artefact.

In accordance with another embodiment of the method according to the invention data preparation takes place prior to the above described analysis and evaluation of the heart frequency information. In a first stage of the data preparation of the intervals $RR_i$ 13 artefacts are identified and eliminated. For this a sliding reference value 21 is calculated from the intervals $RR_i$ 13 and it is determined that an interval $RR_i$ 13 is to be considered as an artefact if it deviates from the previously calculated reference value 21 by more than a pre-determinable percentage, for example more than 30%. As the reference value 21 for an interval $RR_i$ 13 it is allocated the median of the five preceding and five subsequent intervals $RR_i$ 13. In order to calculate the reference value 21 at least a figure of a minimum of three previous and at least three subsequent intervals $RR_i$ 13 should be used. Now, if for an interval $RR_i$ 13 the condition applies that it deviates by more than preferably 30% from its allocated reference value 21, the value of the interval $RR_i$ 13 is replaced by the relevant reference interval 21 (FIG. 8). FIG. 8 shows a sequence of intervals $RR_i$ 13 in accordance with FIG. 3, with the elimination of an artefact being shown by way of example.

In a second date of the data preparation, the method envisages a selection of observation intervals and/or sequences of intervals $RR_i$ 13 for further evaluation. For this an upper limit, for example a predeterminable percentage for artefact frequency of for example 5% is defined and it is determined that observation intervals and/or measuring sections exhibiting an artefact frequency going beyond are excluded from further evaluations. The aforementioned data preparation measures allow the reliability of the analysis results and/or the calculation of the training intensity curve 20 to be improved.

In place of the selection of observation intervals following each other in time or the selection of sequences of intervals $RR_i$ 13 following each other in time, it is also possible that observation intervals that overlap each other in time can be used for analysis and further evaluation and/or calculation of the training intensity curve 20. This has the advantage that a sufficiently high number of points in the training intensity curve 20 in the diagram according to FIG. 6 can be obtained in a shorter time, thereby allowing reliable statements to be derived from the method concerning the current training intensity.

It is also advantageous to take into consideration special incidents during the course of training when selecting the sequence of intervals $RR_i$ 13. A special incident of this type is, for example, a sudden change in the heart frequency HF, as shown in FIG. 3 by the dotted intervals $RR_i$ (for i=5, 6 etc). It is of advantage to select the sequences of intervals $RR_i$ 13 in such a way that such sudden changes in the heart frequency HF are not contained therein. Thus, for example, an initial observation interval 22 (FIG. 3) extends until shortly before the point of the sudden change in the heart frequency HF. During this a subsequent further observation interval 23 only begins after the point of the sudden change in the heart frequency HF. Here it can also be envisaged that a certain number of intervals $RR_i$ 13 that lie in the vicinity of the sudden change in the heart frequency HF are completely excluded from further evaluation. The means that these are not included either in the sequence of intervals $RR_i$ 13 of the first observation interval 22 nor in the corresponding sequence of the further observation interval 23. Furthermore, it can also be envisaged that not only the start and/or end of the observation intervals 23, 23 but also the length and/or the number of intervals $RR_i$ 13 taken into consideration in the observation intervals 22, 23 are adapted, preferably automatically, depending on special incidence occurring during the course of training. These measures for dynamically adapting the analysis boundary conditions have the advantage of better quality and/or increased reliability of the result of analysis.

In accordance with an alternative form of embodiment of the method, it is envisaged that for the analysis of the relevant sequences of intervals $RR_i$ 13 a linear trend elimination is carried out. For this, using the method of the least deviation squares a regression line for the relevant sequence of intervals $RR_i$ 13 is calculated.

$$Y_i = a + bi; \ i = 1 \ldots N$$

The sequence of standardised intervals $rr_i$ 14 is then formed in that from the intervals $RR_i$ 13 the relevant values $Y_i$ are initially subtracted and the obtained value is divided by the mean value $RR_{MV}$ of the intervals $RR_i$ 13

$$rr_i = (RR_i - (a+bi))/RR_{MV}; \ i = 1 \ldots N$$

However, as an alternative to this the sequence of the standardised intervals $rr_i$ 14 can also be generated in that the division is not performed with the mean value $RR_{MV}$, but by the relevant value $Y_i$ of the corresponding regression line $$rr_i = (RR_i - (a+bi))/(a+bi); \ i = 1 \ldots N$$

Through the described linear trend elimination improved stationarity of the standardised intervals $rr_i$ 14 is achieved for which changes in the heart frequency HF and/or intervals $RR_i$ 13 are levelled out right across the observation interval and/or the sequence of intervals $RR_i$.

In accordance with a further alternative example of embodiment of the method, the standardisation/representation of the intervals $RR_i$ 13 takes place on the standardised intervals $rr_i$ 14 using a third degree polynomial. For this, using the method of minimising the deviation squares, a third degree polynomial function is calculated for the sequence of intervals $RR_i$ 13. This means that the sequence of the intervals $RR_i$ 13 is approximated by a third degree polynomial.

$$Y_i = a + bi + ci^2 + bi^3; \ i = 1 \ldots N$$

$$rr_i = (RR_i - Y_i)/Y_i; \ i = 1 \ldots N$$

The sequences of standardised intervals $rr_i$ 14 calculated in the latter described manner are then entered in the same way in a Poincaré plot as set out in FIG. 5. Finally after calculation of the principal longitudinal axis $X_0$ 16 and of the principal vertical axis $Y_0$ 17 the orthogonal distances 18 with regard to the principal longitudinal axis $X_0$ 16 are calculated. The standard deviations $SO_L$ and mean values $RR_{MV}$ of the intervals $RR_i$ 13 and/or the corresponding heart frequencies HF calculated for the selected sequences of intervals $RR_i$ 13 are finally used for calculating the training intensity curve 20. As a result of the standardisation used in this example of embodiment of the intervals $RR_i$ 13 on standardised intervals $rr_i$ 14 there is an even more clearly emphasised increase in the standard deviation $SO_L$ in the higher heart frequencies HF and/or greater stresses range in the intensity curve 20 (FIG. 6).

In yet another alternative form of embodiment of the method, to show the intervals $RR_i$ 13 on the standardised intervals $rr_i$ 14 a Fourier transform is used. Through a Fourier transform intervals $RR_i$ 12 are interpolated by way of determining the coefficients of the Fourier transform. To standardise the intervals $RR_i$ 13 a trigonometric polynomial $F_i$ is finally used, obtained through breaking off the Fourier transform after only a few components. Preferably a trigonometric polynomial consisting of the first three components of the Fourier transform is used to calculate the standardised intervals $rr_i$ 14. The sequence of intervals $RR_i$ 13 is accordingly approximated through the first three components of the Fourier transform.

$$rr_i = (RR_i - F_i)/F_i; \ i=1 \ldots N$$

The further analysis of the sequence of intervals $RR_i$ 13 and/or the standardised intervals $rr_i$ 14 takes place as set out above through entering the standardised intervals $rr_i$ 14 into a Poincaré plot in accordance with FIG. 5 and calculating the standard deviation $SO_L$ from the orthogonal distances 18 of the points in the Poincaré plot with regard to the principal horizontal axis $X_0$ 16. From this points on the training intensity curve 20, as set out in FIG. 6, are calculated and used for assessing the current training intensity of the person 2.

In a further embodiment of the method in accordance with the invention it is also possible to use, after standardisation of the intervals $RR_i$ 13, series developments employing so-called wavelets or wavelet transformations. Of the thereby obtained series developments only a few components are used to form a polynomial $W_i$. Preferably the first three components of the wavelet series development of the intervals $RR_i$ 13 are used for standardisation.

$$rr_i = RR_i - W_i/W_i; \ i=1 \ldots N$$

All details of value ranges in this description should be understood in the sense that these also include any and all partial ranges thereof, e.g. the indication 1 to 10 should be taken to mean that all partial ranges, starting from the lower limit 1 and the upper limit 10, are included, i.e. all partial ranges start with a lower limit of 1 or greater and end with an upper limit of 10 or lower, e.g. 1 to 1.7, or 3.2 to 8.1 or 5.5 to 10.

The examples of embodiment describe possible variant embodiments of the method, whereby it should be noted at this point that the invention is not limited to the specially illustrated examples of embodiment thereof, but rather that various combinations of the individual variations of embodiment are possible and this variation possibility is within the technical field of a person skilled in the art on the basis of the technical teaching by the present invention. Therefore all conceivable embodiment variations that are possible through combinations of individual details of the illustrated and described embodiment variations are also covered by the protective scope.

For the sake of good order it is finally also pointed out that for a better understanding of the structure of the device 1, the components parts have in places been shown not to scale and/or in enlarged or reduced form.

The underlying objective of the independent inventive solutions can be gleaned from the description.

Above all, the individual embodiments shown in FIGS. 1, 2; 3, 4, 5, 6, 7 and 8 can form the subject matter of independent solutions in accordance with the invention. The relevant inventive objectives and solution are set out in the detailed descriptions of these figures.

List of References

1 Device
2 Person
3 Chest belt
4 Sensor
5 Monitoring unit
6 Transmitter
7 Receiver
8 Control unit
9 Evaluation unit
10 Memory
11 Operating unit
12 Display
13 Interval $RR_i$
14 Interval $rr_i$
15 Points cluster
16 Principal horizontal axis $X_0$
17 Principal vertical axis $Y_0$
18 Distance
19 Distance
20 Training intensity curve
21 Reference value
22 Observation interval
23 Observation interval

The invention claimed is:

1. A method of determining the training intensity of a person, whereby the heart frequency data of the person is measured, the method comprising:
   a) recording the time intervals $RR_i$ between consecutive heartbeats;
   b) selecting a sequence of intervals RR through defining a number N of consecutive intervals $RR_i$ or determining an observation interval;
   c) producing a sequence of standardized intervals $rr_i$ from the sequence of intervals $RR_i$ through mathematical modelling;
   d) creating points in a Poincaré plot of the standardized intervals $rr_i$ from two consecutive standardized intervals $rr_i$ and $rr_{i+1}$;
   e) calculating a 95% confidence ellipse for the points of the sequence of standardized intervals $rr_i$ in the Poincaré plot, whereby a principal horizontal axis $X_0$ and a principal vertical axis $Y_0$ is determined;
   f) calculating a standard deviation $SO_L$ from the orthogonal distances of the points of the sequence of standardized intervals $rr_i$ with regard to the principal horizontal axis $X_0$;
   g) storing a pair of values consisting of a mean value $RR_{MV}$ of the sequence of intervals $RR_i$ and the standard deviation $SO_L$;
   h) selecting further sequences of intervals $RR_i$ and for these further sequences of intervals $RR_i$ the steps c) to g) are carried out;
   i) producing a training intensity curve from the pairs of values, determined in steps c) to h) of the heart frequencies HF (HF =$1/RR_{MV}$)corresponding to the mean values $RR_{MV}$ and standard deviations $SO_L$; and j) through comparing the most recently determined heart frequency HF with the training intensity curve a current, specific training intensity is determined for the person.

2. The method according to claim 1 wherein the sequences of intervals $RR_i$ envisaged for analysis are selected depending on incidents during the course of training.

3. The method according to claim 2, wherein the sequences of the intervals $RR_i$ are selected in such a way that points of sudden change in the heart frequency HF are excluded or not included.

4. The method according to claim 1 wherein the sequences of the intervals $RR_i$ for analysis are selected from observation intervals that overlap each other in time.

5. The method according to claim 1 wherein in order to identify and eliminate artifacts in the selected sequence of intervals $RR_i$, a reference value is assigned to each interval $RR_i$ whereby the reference value is formed by a median of the at least three preceding and the at least three subsequent intervals $RR_i$, and if the selected interval $R_i$ deviates from its assigned reference value by more than a first predeterminable percentage, this interval $RR_i$ is replaced by its reference value.

6. The method according to claim 5, wherein 30% is selected as the first percentage.

7. The method according to claim 5, wherein observation intervals that exhibit an artifact frequency going beyond a limit of a second predeterminable percentage are excluded from further evaluation.

8. The method according to claim 7 wherein 5% is selected as the second percentage.

9. The method according to claim 1 wherein to generate the sequence of standardized intervals $rr_i$ each interval $RR_i$ is divided by a mean value $RR_{MV}$ of the sequence of intervals $RR_i$ in accordance with the formula $rr_i=RR_i/RR_{MV}$; i=1 ... N.

10. The method according to claim 9, wherein in order to generate the sequence of standardized intervals $rr_i$ a linear trend elimination with a regression line ($Y_i=a+b\ i$) is also carried out for the sequence of intervals $RR_i$ in accordance with the formula $rr_i=(RR_i-(a+b\ i))/RR_{mw}$; i=1 ... N.

11. The method according to claim 1, wherein in order to generate the sequence of standardized intervals $rr_i$ an approximation of the sequence of intervals $RR_i$ through a regression line ($Y_i=a+b\ i$) is used in accordance with the formula $rr_i=(RR_i-(a+b\ i))/(a+b\ i)$; i=1 ... N.

12. The method according to claim 1, wherein in order to generate the sequence of standardized intervals $rr_i$ an approximation of the sequence of intervals $RR_i$ by a third degree polynomial ($Y_i=a+b\ i+c\ i^2+b\ i^3$) is used in accordance with the formula $rr_i=(RR_i-(a+b\ i+c\ i^2+b\ i^3))/(a+b\ i+c\ i^2+b\ i^3)$; i=1 ... N.

13. The method according to claim 1, wherein in order to generate the sequence of standardized intervals $rr_i$ an approximation of the sequence of intervals $RR_i$ by trigonometric polynomial $F_i$ consisting of the first three components of a Fourier transform is used in accordance with the formula $rr_i=(RR_i-F_i)/F_i$; i=1 ... N.

14. The method according to claim 1 wherein in order to generate the sequence of standardized intervals $rr_i$ an approximation of the sequence of intervals $RR_i$ by the first three components of a wavelet series development $W_i$ is used in accordance with the formula $rr_i=(RR_i-W_i)/W_i$; i=1 ... N.

15. The method according to claim 1 wherein as the training intensity curve is an approximation of the pairs of values consisting of a heart frequency HF and the standard deviation $SO_L$, or an approximation of the pairs of values consisting of the heart frequency HF and the quotient $s=SO_L/SO_W$ is used in accordance with the formula of a, preferably third-degree, polynomial, $SO_L(HF)=s_0+s_1HF+s_2HF^2+s_3HF^3$ or $s(HF)=u_o+u_1HF+u_2HF^2+u_3HF^3$.

16. The method according to claim 15 wherein the training intensity curve is recalculated at regular time intervals.

17. The method according to claim 1 wherein the training intensity curve is saved on completion of the training along with data such as the name of the person and the dates of the completed training.

18. The method according to claim 1, further comprising:
a) storing a pair of values consisting of a mean value $RR_{mv}$ of the sequence of intervals $RR_2$ and a quotient $s=SO_L/SO_W$ formed of the standard deviation $SO_L$ and the standard deviation $SO_W$; and
b) producing a training intensity curve from the pairs of values, determined in steps c) to h) of the heart frequencies HF (HF =$1/RR_{mv}$) corresponding to the mean values $RR_{vrj}$ and the quotient s formed of standard deviations $SO_L$ and standard deviations $SO_W$.

19. A device for monitoring the stress intensity of a person comprising a unit attachable to the person with a sensor for recording heartbeats wherein the device comprises an evaluation unit with means for implementing a method in accordance with claim 1 and an output unit for informing the person of the determined stress intensity.

* * * * *

UNITED STATES PATENT AND TRADEMARK OFFICE
CERTIFICATE OF CORRECTION

PATENT NO. : 8,401,630 B2  
APPLICATION NO. : 12/526114  
DATED : March 19, 2013  
INVENTOR(S) : Nikolaus Klepp

Page 1 of 1

It is certified that error appears in the above-identified patent and that said Letters Patent is hereby corrected as shown below:

In the Claims

Col. 12, line 39, "$RR_{yrj}$" should read -- $RR_{MV}$ --.

Signed and Sealed this  
Twenty-fifth Day of November, 2014

Michelle K. Lee  
*Deputy Director of the United States Patent and Trademark Office*